United States Patent
Carraher et al.

(10) Patent No.: US 11,623,909 B2
(45) Date of Patent: Apr. 11, 2023

(54) WATER-BASED EXTRACTION AND PURIFICATION PROCESSES FOR CANNABINOID ACIDS

(71) Applicant: MEDPHARM IOWA LLC, Des Moines, IA (US)

(72) Inventors: Jack McCaslin Carraher, Nevada, IA (US); Zach Joseph Baker, West Des Moines, IA (US)

(73) Assignee: MEDPHARM IOWA LLC, Des Moines, IA (US)

( * ) Notice: Subject to any disclaimer, the term of this patent is extended or adjusted under 35 U.S.C. 154(b) by 353 days.

(21) Appl. No.: 16/994,378

(22) Filed: Aug. 14, 2020

(65) Prior Publication Data

US 2021/0053902 A1 Feb. 25, 2021

Related U.S. Application Data

(60) Provisional application No. 62/890,355, filed on Aug. 22, 2019.

(51) Int. Cl.
| | |
|---|---|
| *C07C 51/50* | (2006.01) |
| *C07C 51/44* | (2006.01) |
| *C07D 311/80* | (2006.01) |

(52) U.S. Cl.
CPC ............ *C07C 51/50* (2013.01); *C07C 51/445* (2013.01)

(58) Field of Classification Search
None
See application file for complete search history.

(56) References Cited

U.S. PATENT DOCUMENTS

| | | | |
|---|---|---|---|
| 9,376,367 B2 | 6/2016 | Herkenroth et al. |
| 10,941,102 B2 | 3/2021 | Wohleb et al. |
| 2018/0147247 A1 | 5/2018 | Ivanov |
| 2019/0020738 A1 | 1/2019 | Paul et al. |
| 2019/0160393 A1 | 5/2019 | Marshall et al. |

OTHER PUBLICATIONS

Patent Cooperation Treaty, "International Preliminary Report on Patentability," issued in connection with International Patent Application No. PCT/US2020/046524, dated Mar. 3, 2022, 7 pages.
International Searching Authority, "Search Report and Written Opinion," issued in connection to International Patent Application No. PCT/US2020/046524, dated Nov. 10, 2020, 7 pages.
International Searching Authority, "International Preliminary Report on Patentability," issued in connection to International Patent Application No. PCT/US2020/046524, dated Feb. 17, 2022, 6 pages.

*Primary Examiner* — Zinna Northington Davis
(74) *Attorney, Agent, or Firm* — Nyemaster Goode P.C.

(57) ABSTRACT

The present invention relates to methods of extracting cannabinoid acids from cannabis plant material by combining the plant material with an aqueous solution having a high pH to solubilize cannabinoid acid anions, followed by precipitation of the cannabinoid acids at low pH and filtration. The method provides yields of up to 97%, while high pH purification of ethanol extracted oils yielded purities up to 86%.

14 Claims, 5 Drawing Sheets

Figure 3:
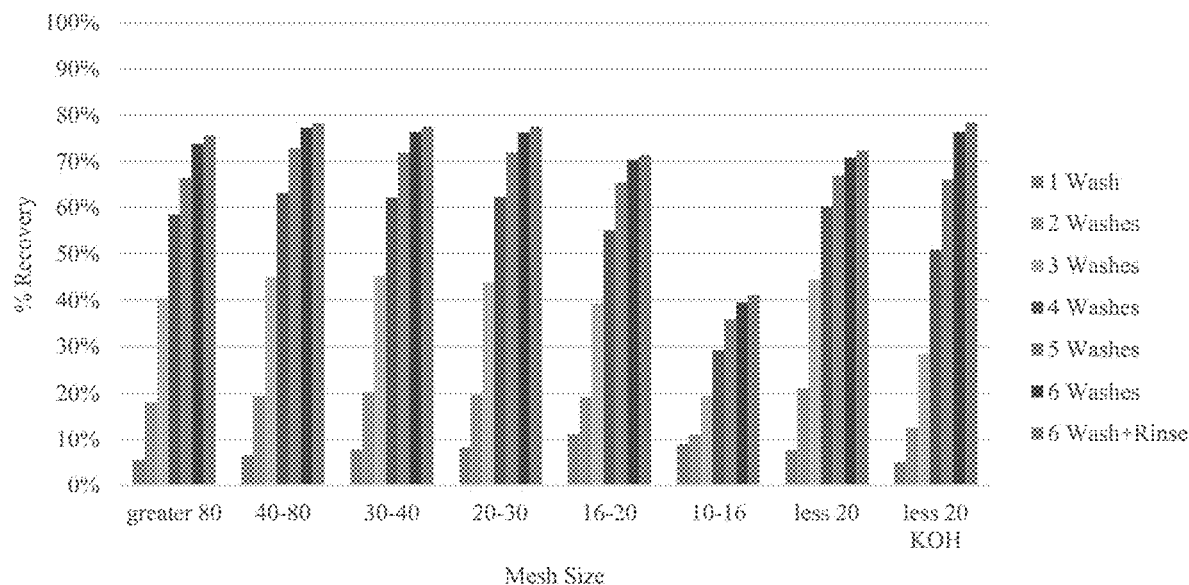

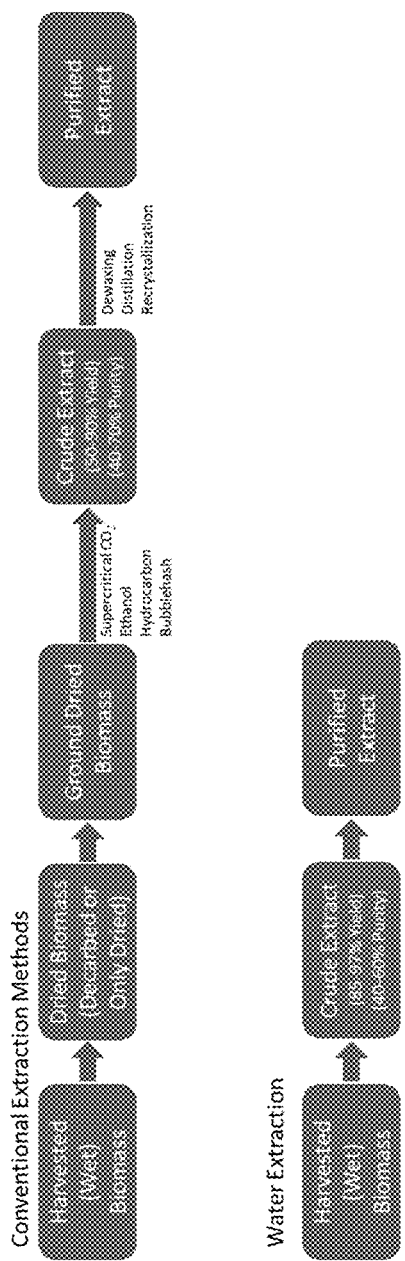
FIG 1.
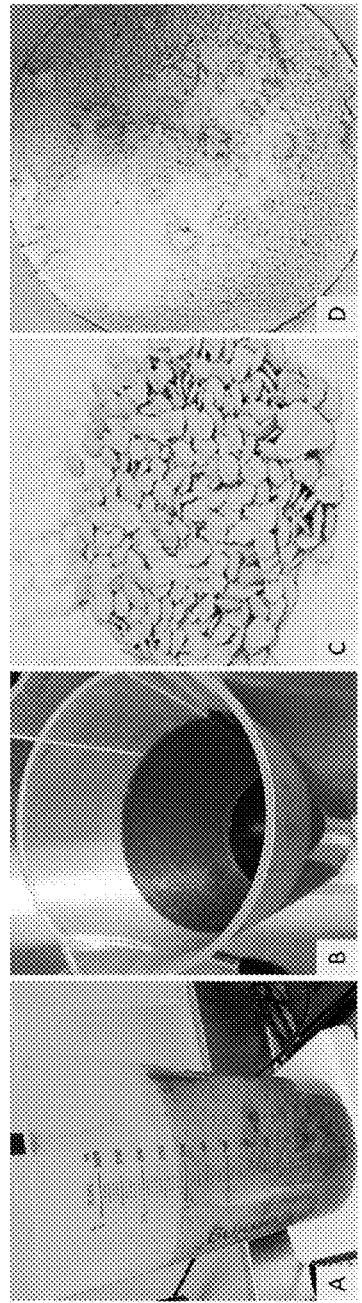
FIG. 2A-D

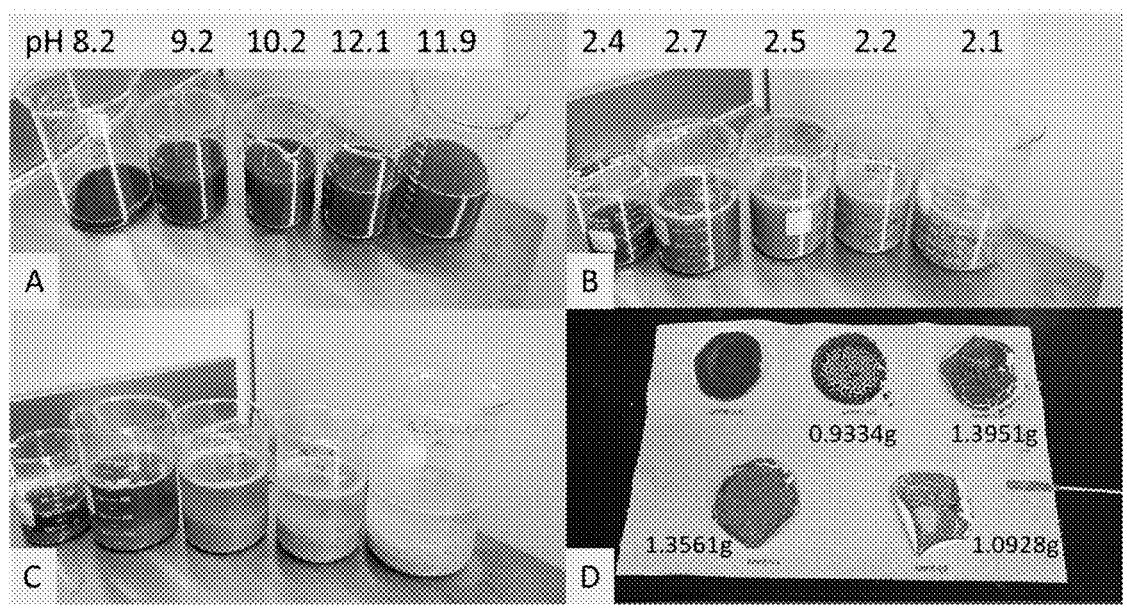
FIG. 7A-D
Raw Aqueous Extract | Salted Out Mixture 0.3174g solids | Filtrate After Salting | pH 2.2 0.2403g solids
FIG. 8A-D

WATER-BASED EXTRACTION AND PURIFICATION PROCESSES FOR CANNABINOID ACIDS

CROSS REFERENCE TO RELATED APPLICATIONS

This application claims the benefit of priority to U.S. Provisional Patent Application No. 62/890,355, filed Aug. 22, 2019, entitled "WATER-BASED EXTRACTION AND PURIFICATION PROCESSES FOR CANNABINOID ACIDS," the entire disclosure of which is hereby incorporated by reference in its entirety.

BACKGROUND OF THE INVENTION

Common methodologies for extraction of cannabinoids from cannabis materials utilize solvents (chiefly ethanol), liquid propane or butane, supercritical $CO_2$, or cold water with a series of sieves (bubble hash) methods. In order to obtain high concentration distillates (80-97%) from any of these methods, one must dewax at low temperature in ethanol overnight, collect the ethanol by rotary evaporation, and distill the dewaxed oil under vacuum. Achieving high purity (>90%) neutral cannabinoids often requires distillation multiple times. Yields from each iteration of distillation can range from 30-70% due to degradation of cannabinoids at the high temperatures required for volatilization. Alternatively, cannabinoid acid crystals can be formed by subjecting a saturated solvent to low temperature for long periods of time (FIG. 1).

Bubble hash is a product prepared by mechanical abrasion of cannabis flower in an ice bath to knock off trichomes. The flower is placed in a series of bags with different mesh sizes and then placed in an ice-cold water bath. The ice acts as an abrasive agent. The purity of the final material is dependent upon which sieve bag it is found in after draining the water. A good yield by this method is around 10% by weight with a purity of about 50%. However, the yield of cannabinoid is likely under 5%.

Each of these described methods have certain disadvantages. For instance, while organic solvents offer fast extraction, they are expensive and hazardous (particularly at large scale). Supercritical fluids are cleaner extraction methods but are difficult to scale due to extreme extraction conditions and expensive equipment. Natural gas extractions are cheaper and fast but are particularly unsafe due to their flammable nature and the presence of residual gas in the finished products. The collection of trichomes by way of bubble hash processing yields a product free of harmful solvents but, as noted, has low yields.

All of these current methods require dewaxing, solvent recovery, and distillation in order to obtain high purity materials. While one could utilize chromatography for purification, this would require significant amounts of organic solvents and therefore increase expense and may require explosion proof equipment at larger scales.

There is therefore a continued need to develop a cost-effective process for extracting cannabinoids from cannabis plant material which provides high yields and high purity cannabinoid acids.

SUMMARY OF THE INVENTION

The present invention relates to methods for extracting cannabinoids from cannabis plant material that utilizes aqueous solutions at high pH to solubilize cannabinoid acid anions for extraction followed by precipitation of protonated cannabinoid acids at low pH and filtration. Also included is purification of ethanol extracts with high pH water solutions. Extraction yields up to 97% were obtained with direct extraction into high pH water (typical crude purity 30-60% cannabinoid acid). Purification of ethanol extracted material with high pH water yielded up to 57% with purities up to 86%.

The aqueous extraction methods of the present invention are lower in both capital and operational cost than traditional extraction methods and are faster, especially when compared to the traditional methods of extraction, dewaxing, solvent collection, and distillation with recrystallization if isolated cannabinoid is desired as each of these steps may require days to obtain a single kg of distillate/isolate. Further, the method is scalable, more environmentally friendly, and yields high purity products that are safer for human and animal consumption due to the lack of residual organic solvents.

The highly purified cannabinoid acids that are obtained by these methods can be used directly, esterified by standard methods, or thermally or chemically decarboxylated to yield high purity isolates (like CBD, CBG, CBN and other cannabinoids that are solids at room temperature) or high purity distillates of THC (or other cannabinoids that are oils at room temperature) that can be obtained without dewaxing, recovery of solvent, and/or distillation.

DETAILED DESCRIPTION OF THE FIGURES

FIG. 1 is a flow chart showing traditional processing of cannabis-containing plants for extraction of cannabis and one for the water-based method in accordance with the present invention.

FIG. 2A-D is a set of images showing water-based purification of an ethanol extracted crude oil: Aqueous solution B1 of ethanol extracted cannabis oil at pH 8 with oil deposits on polypropylene pitcher (A). Oil deposits from solution C2 on polypropylene pitcher after being allowed to sit overnight at pH 11 (B). 77% pure THCA from solution C1 (C). 87% pure THCA (D).

FIG. 3 is a chart showing CBDA recovery as a function of biomass particle size after multiple 10-minute washes of ground biomass with 40 ml pH 11.9 solutions (NaOH) followed by one rinse with water (no NaOH). One experiment with KOH is shown.

Figure 4:
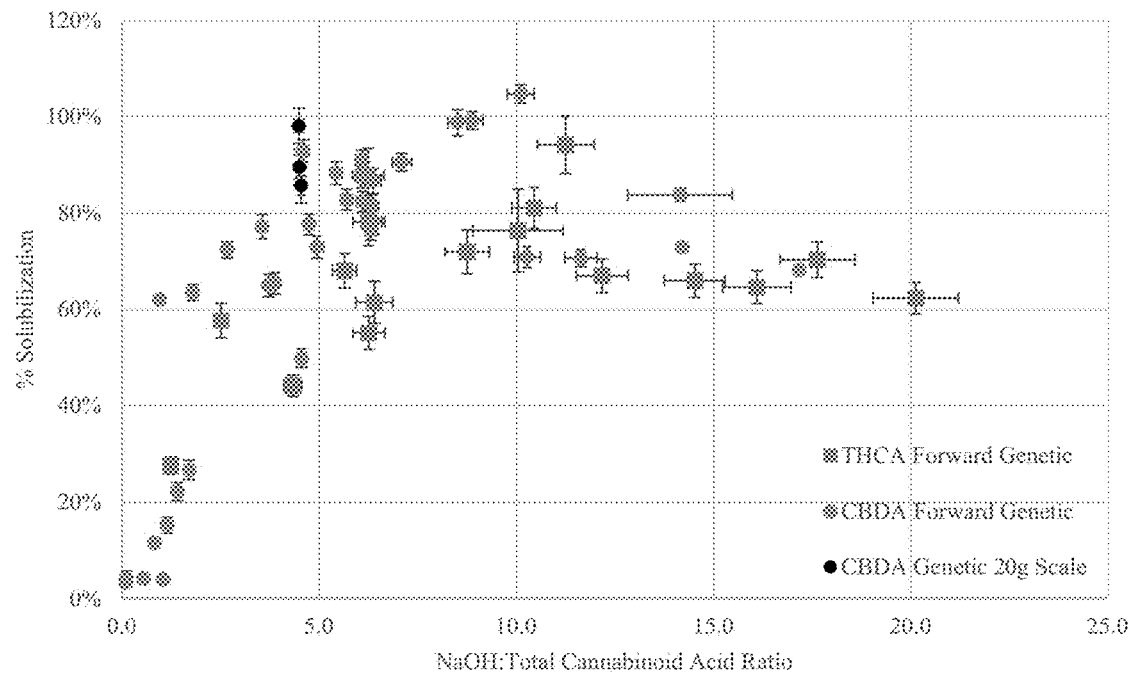

FIG. 4 is a chart showing the first wash solubilization (represented as % of initial CBDA present in the biomass) as a function of NaOH:total cannabinoid acid (mol:mol) ratio, with percentage Solubilization vs NaOH:(CBDA+CBGA+THCA) for the first wash at room temperature for CBDA forward biomass at 1 g scale (orange circles), CBDA forward biomass at 20 g scale (black circles) and THCA forward biomass at 300 mg scale (blue squares). Error bars were calculated from the initial total cannabinoid range (x-axis) and initial CBDA or THCA percentages (y-axis) relative to the average potency values. Starting CBDA forward biomass contained 5.8-7.2% CBDA and 6.2-7.6% total cannabinoid acid (CBDA+CBGA+THCA) and THCA forward biomass contained 18.1-22.4% THCA and 18.6-23.2% total cannabinoid acid (CBDA+CBGA+THCA).

Figure 5A:
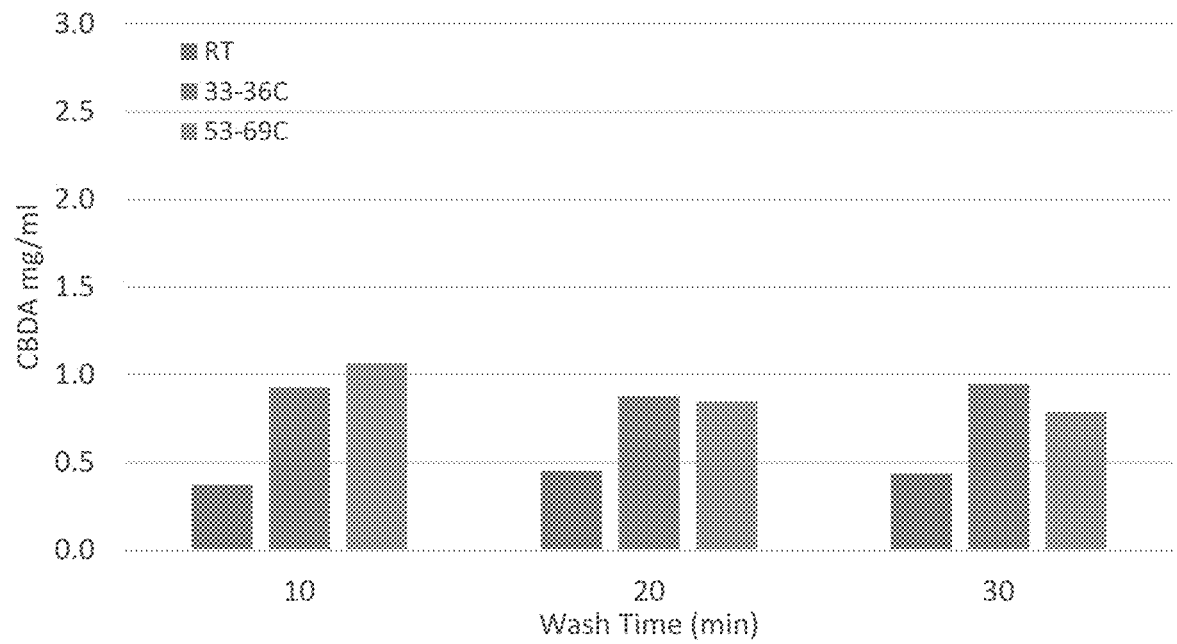
Figure 5B:
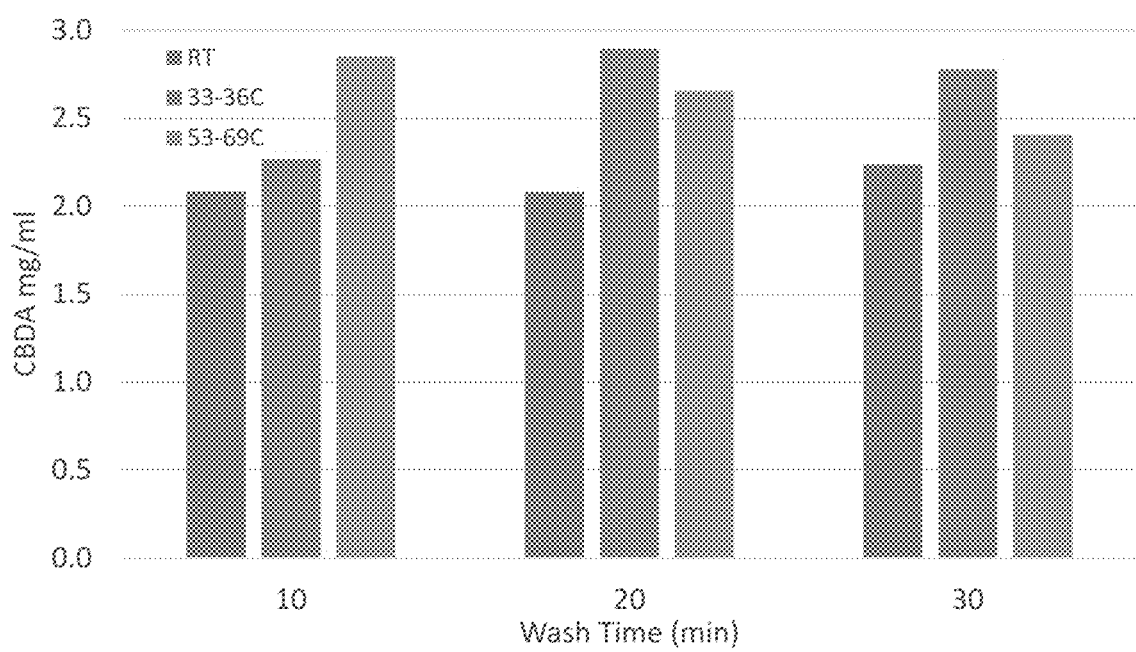
Figure 5C:
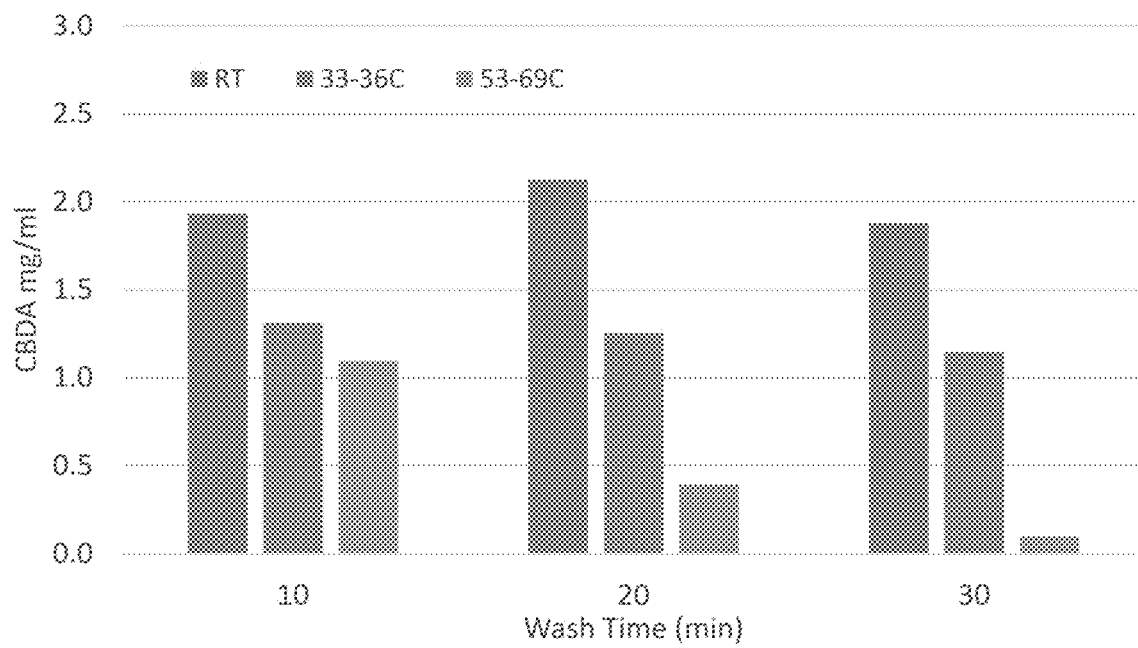

FIG. 5A-C depict the amount of CBDA in solution (mg/ml) at room temperature, 33-36° C. and 53-69° C. at pH 12.0 (FIG. 5A), 12.5 (FIG. 5B) and 13.0 (FIG. 5C).

Figure 6:
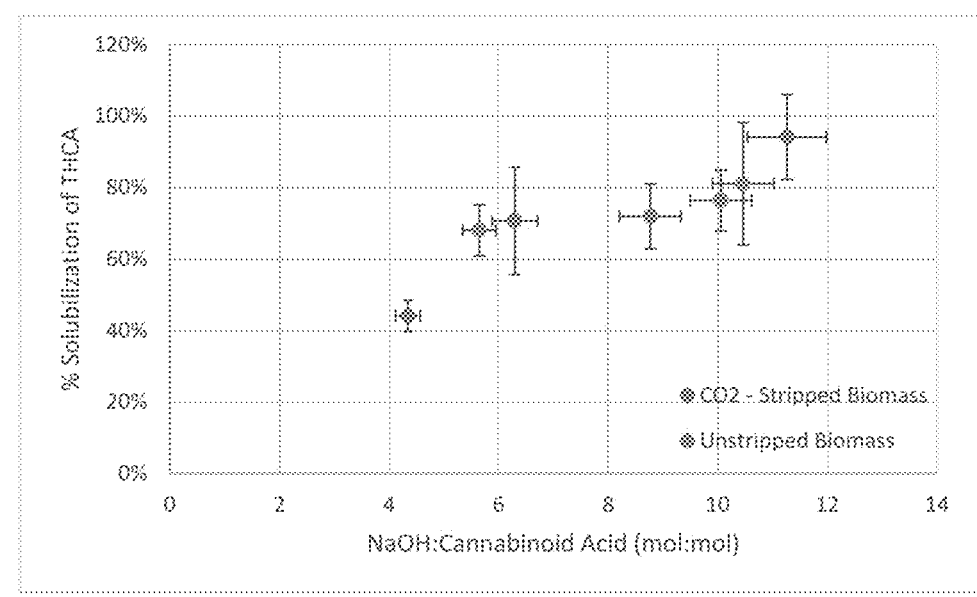

FIG. 6 is a chart showing the first wash solubilization of THCA vs. NaOH:total cannabinoid acid (mol:mol) ratio for $CO_2$-stripped and non-stripped biomass, with the plot of first wash solubilization of THCA (%) vs NaOH:(CBDA+CBGA+THCA) mol:mol ratio for $CO_2$-stripped (blue) and dried (orange) ground cannabis flower. Error bars were calculated from uncertainty in the initial biomass (x and y) and standard deviation when multiple experiments of a similar ratio were run (y only).

FIG. 7A-D is a set of images of water extracted THCA at an NaOH:total cannabinoid acid ratio of 1:1 before acidification, after acidification and after filtration, where FIG. 7A depicts 1:1 NaOH:THCA aqueous extractions (experiment A-1-5) after separation of extract from plant material, FIG. 7B depicts acidification to pH 2-3, FIG. 7C depicts allowing the precipitate to settle, and FIG. 7D depicts filtration of the precipitate.

FIG. 8A-D is a set of images for NaCl-based purification of the water-extracted THCA solution, where FIG. 8A depicts 1:1 NaOH:THCA aqueous extraction (experiment A-6) followed by NaCl cleanup (A-7) after separation of extract from plant material, FIG. 8B after addition of 40 g NaCl, FIG. 8C after filtration of NaCl precipitate, and FIG. 8D depicts acidification to pH 2-3.

DETAILED DESCRIPTION OF THE INVENTION

The present invention describes extraction of cannabinoids from cannabis plant material that utilizes aqueous solutions at high pH to solubilize cannabinoid acid anions for extraction followed by precipitation of protonated cannabinoid acids at low pH and filtration. (FIG. 1). It has now been determined that water extraction is possible when sufficient amounts of sodium hydroxide or other strong or weak inorganic or organic base(s) are utilized.

The cannabinoids may be extracted from any source of plant material that contains cannabinoid acids including, but not limited to, cannabis, Coneflower (*Echinacea*), Electric Daisy (*Acmella oleracea*), Japanese Liverwort (*Radula marginata*), Helichrysum (*Helium italicum*), and *Cacao* (*Theobroma cacao*). The plant materials may be wet whole plant material, dried whole plant material, wet flower and trim, or dried flower and trim. It may be unground or ground and sieved or not. The material may have been heated to decarboxylate the cannabinoid acids prior to extraction, preferably not. Further, the plant materials may optionally go through a pre-extraction procedure with subcritical (and/or supercritical) $CO_2$ to capture valuable terpenes and to extract neutral cannabinoids and other impurities. The method may also be used for aqueous purification of solvent, $CO_2$, or natural gas extracted crude oils.

The extraction procedure involves placing one or more sources of cannabinoids in a reactor along with an aqueous solution of a base, such as sodium hydroxide, for instance in a molar ratio of between about NaOH:cannabinoid acid 0.5:5 to about 10:0.5 to a pH typically 12 or higher to efficiently solubilize the cannabinoid acid anions. In one embodiment, the pH is from about 10-13 and the NaOH concentration is from about 200 mg/l to about 4000 mg/l. Any inorganic or organic base may be used in this step so long as it provides the necessary pH to the solution and is compatible with the other ingredients. Such bases include, but are not limited to, metal hydroxides, such as sodium hydroxide, potassium hydroxide, lithium hydroxide, and calcium hydroxide, metal oxides, such as sodium oxide, magnesium oxide, and copper (II) oxide, and organic bases, such as ammonia, trimethyl amine, triethyl amine, pyridine, sodium acetate, sodium citrate, and others. The amount of base required for high efficiency extraction from the first wash is directly proportional to the total amount of cannabinoid acid in the starting biomass. A mol:mol ratio of NaOH:(CBDA+THCA+CBGA) on the order of 5-12 achieved the highest solubilization of target molecules in the first wash. The specific pH and volume are irrelevant provided the mol:mol ratio of base:acid is within the range 5-12. Extractions with base:acid ratios up to 52:1 were successful, but resulted in lower yields due to degradation of the target compounds. Extractions below the range achieved lower yields within the first wash, but additional material could be obtained by repeated washing with high pH water.

The mixture is then optionally stirred or agitated or simply allowed to sit, for instance at least 10 minutes. The aqueous solution is separated from the undissolved plant material and acidified to form a precipitate comprising protonated cannabinoid acid. In one embodiment of the invention, the mixture is allowed to sit overnight. The solution is filtered and acidified to form a precipitate that is then filtered from the wash. The extraction wash may be repeated multiple times to increase the yield of cannabinoid acid. Successive washes may be as short as 1 minute or as long as 10 minutes or greater. The extract may be filtered or centrifuged once or multiple times to achieve higher degrees of purity. First wash cannabinoid acid recovery was proportional to the relative volume of wash solution recovered; which was limited by the amount of wash remaining associated with the biomass. Additional recovery was achieved through additional washings of 1-10 minutes in length with aqueous solutions of the same or different amounts of base. Each additional wash yielded an amount of cannabinoid acid that was proportional to the dilution factor of the new wash relative to the solution retained in the biomass after the previous wash, i.e. if 1 part of wash remains with the biomass and 9 parts of fresh solution are added then 9/10 of the remaining cannabinoid acid can be recovered from the second wash, and a third wash of the same volume would recover an additional 9% of the remaining cannabinoid acid, etc. . . . . The majority of the cannabinoid acid can be recovered after only 2 rinses with high pH water. Utilizing water with no added base in the subsequent washes also recovers cannabinoid acids but with reduced efficiency.

Pre-treatment of the biomass may include, but is not limited to, drying, determining, grinding, decarboxylation, or pre-extraction (stripping of terpenes and other impurities) by $CO_2$ or another selective solvent. None of the above biomass treatment techniques were found to be necessary for efficient extraction provided the base:acid ratio was within the range described above. High moisture content within the biomass was found to result in higher yields from the first wash. This is directly related to the amount of wash retained by the biomass upon separation of the wash and the biomass. The first wash solubilization was not affected by the material's initial moisture content. An inverse relationship between cannabinoid content (by weight) and particle size was observed upon grinding. However, extraction efficiency of non-sieved ground biomass was independent of particle size and extraction of unground cannabis flower achieved similar results. $CO_2$-stripped biomass exhibited a similar first wash solubilization (as a function of base:acid ratio) to non-stripped material (FIG. 10).

The extraction easily scaled from 0.3-1 g to 20 g without requiring modification to the previously determined optimal parameters. Scaling to multiple kg of biomass is expected to yield similar results.

In at least one embodiment of the present invention, the basic extract may optionally be further purified by acidification to a pH range of from about 6-9, and in at least one embodiment the pH is 8. Acids appropriate for this purpose are any acids compatible with the other ingredients of the extract and which provide the appropriate level of acidity to the basic solution. Such acids include, but are not limited to, hydrochloric acid, nitric acid, chloric acid, sulfurous acid, phosphoric acid, nitrous acid, hydrofluoric acid, benzoic acid, acetic acid, and formic acid.

Instead of or in addition to adding acid to purify the basic extract, the basic extract may be allowed to sit for a length of time sufficient to separate the hydrophobic impurities followed by filtering, or by simply filtering the extract directly. In either instance, the extract may be run through a hydrophobic filter, such as a polypropylene filter, sand, glass beads, or other similar materials that may behave as sorbents or flocculants. These adsorbed impurities may be collected with an ethanol wash and distilled to yield additional terpenes and neutral cannabinoids. The cannabinoid acids are harvested from the purified filtrate by acidification to about pH 2-3 followed by filtration of the precipitate and washing with water or acidified water at or around pH 4-5.

As cannabinoid acids cannot be distilled (as they will decarboxylate) they can be purified by the addition of NaCl or other halide salts, such as NaBr, NaI, KCl, KBr, etc. to the filtrate or to the basic extract, and filtered. Other types of salts, such as sulfates, phosphates, carbonates, acetates, etc. may also work for this purpose. In one embodiment of the invention, the salts are added in a concentration of from about 5-10% by weight. The cannabinoid acids are solubilized by the increasing ionic strength of the solution from the salt while maintaining an optimized pH. The added salt also precipitates out plant-based impurities leaving the impurities with the original plant material. The precipitated and filtered cannabinoid acids can be further purified by repeated acid-base cycles or by recrystallization in an organic solvent. The highly purified cannabinoid acids can be decarboxylated using conventional methods to yield high purity isolates (like CBD, CBG, CBN and other cannabinoids that are solids at room temperature) or high purity "distillates" of THC (or other cannabinoids that are oils at room temperature), all without the necessity of dewaxing, recovery of solvent, and/or distillation.

The following examples are offered to illustrate but not limit the invention. Thus, it is presented with the understanding that various formulation modifications as well as method of delivery modifications may be made and still are within the spirit of the invention.

Example 1

Water Extraction of Cannabinoid Acids

Preliminary Water Extraction of THCA from $CO_2$ Extracted Oil Experiments

A 15 g aliquot of warmed (55° C.) 180809DD (~10.8 g THCA) was combined with 5 ml 3.2M aqueous NaOH (NaOH:THCA 1.05:1 mol:mol), then vortexed in a centrifuge tube. The mixture was centrifuged for 10 minutes at 4300 RPM and 4.5 g of aqueous solution was decanted. The aqueous solution was acidified and 0.7 g of a white precipitate was collected. This procedure was repeated with minimal collection of additional precipitate; however, it was determined that optimal separation required using hot cannabis oil.

The second attempt utilized ethyl acetate to dissolve the cannabis oil (11.26 g oil in 5 ml EtOAc) followed by liquid-liquid extraction with 25 ml of 10 wt % KOH water. The solution was of a single phase upon mixing. Only upon addition of HCl did phase separation occur. The mixture eventually became triphasic with no THCA in the aqueous phase (middle) and the remainder relatively evenly distributed amongst a heavy oil phase (bottom) and the ethyl acetate phase (top).

Sub- & Supercritical $CO_2$ Extraction (Stripping) of High THCA Containing Biomass:

Harvested material was not decarboxylated as per usual protocol and was instead dried at 110° F. under −26 to −29 in Hg vacuum for 20 hours. The resulting 26.82 kg of the high THC/THCA containing genetic was run through MPI's supercritical $CO_2$ extractor from Apex (see Table 1). The extractions consisted of 6×4-5 kg runs. Most runs consisted of a subcritical (900-1000 psi & 60-70° F.) extraction for 60-80 minutes followed by a supercritical extraction (2800-3000 psi & 110° F.) for 229-345 minutes. The yield of THCA from initial extraction ranged from 2.6-3.8 wt % (16-24% extraction efficiency). The $CO_2$ extractions were done to remove terpenes and THC from the plant material in an effort to yield material with THCA and minimal THC. Methanol extraction and HPLC analysis on the 'spent' material revealed a range of 0.4-17.1 wt %, however, it was discovered that there were significant inconsistencies in spent samples within a given run. Therefore, for the purposes of this disclosure the average difference (initial THCA-extracted THCA) was used for the initial conditions of the spent material. These values ranged from 10.8-13.4 wt % (Ave(std dev)=12.3(0.9)%) relative the total mass of spent material.

TABLE 1

$CO_2$ extraction conditions and yields for dried (non-decarboxylated) material

| | Initial Mass (kg) | Phase 1 Oil Mass (g) | Phase 2 Oil Mass (g) | Total Oil Mass (g) | Oil Purity | Spent Dried Mass (kg) | wt % THCA Extracted | wt % THCA Initial |
|---|---|---|---|---|---|---|---|---|
| 1 | 5.000 | 132.7 | 285.0 | 417.7 | 49.5% | 4.610 | 2.57% | 15.92% |
| 2 | 5.000 | 114.7 | 315.0 | 429.7 | 50.8% | 4.575 | 3.33% | 15.92% |
| 3 | 4.750 | 123.8 | 265.0 | 388.8 | 55.6% | 4.380 | 3.00% | 15.92% |
| 4 | 4.000 | 240.0 | 170.0 | 410.0 | 65.7% | 3.635 | 5.10% | 15.92% |
| 5 | 4.000 | 70.0 | 260.0 | 330.0 | 59.5% | 3.675 | 3.69% | 15.92% |
| 6 | 4.070 | 94.5 | 285.0 | 379.5 | 53.1% | 3.745 | 3.77% | 15.92% |

TABLE 1-continued

| | | CO$_2$ Extraction Conditions | | | | | | |
|---|---|---|---|---|---|---|---|---|
| | Phase 1 | | | | Phase 2 | | | |
| | Time (min) | Pressure (psi) | Chiller 1 Temp (° F.) | Chiller 2 Temp (° F.) | Time (min) | Pressure (psi) | Chiller 1 Temp (° F.) | Chiller 2 Temp (° F.) |
| 1 | 80 | 900 | 60 | 90 | 229 | 3000 | 110 | 95 |
| 2 | 60 | 1000 | 70 | 95 | 345 | 3000 | 110 | 95 |
| 3 | 70 | 950 | 65 | 95 | 290 | 3000 | 110 | 100 |
| 4 | 80 | 3000 | 110 | 100 | 260 | 3000 | 110 | 100 |
| 5 | 60 | 950 | 65 | 90 | 271 | 3000 | 110 | 100 |
| 6 | 60 | 910 | 60 | 90 | 301 | 2800 | 110 | 100 |

Ethanol Extraction of Spent Material & Water Purification:

Ethanol is a standard extraction solvent in the cannabis industry. A 900 g portion of the 'spent' high THC/THCA material was placed in a food grade 5 gal bucket and filled to the ¾ mark (4.15 l) with ethanol. The mixture was stirred with an overhead mixer with a propeller mixing blade at ~1000 RPM for 10 minutes. 3.020 kg of ethanol filtrate was recovered after filtration with a Buchner funnel and filter paper. The ethanol extraction was repeated twice more with 4.070 and 4.115 kg ethanol yielding 3.805 & 4.550 kg of filtrate, respectively. HPLC analysis indicated that a total of 119.1 g of THCA could be found in the filtrate (see Table 2). The remaining undissolved plant material was found to contain 0.18 wt % THCA indicating a very high extraction efficiency (~98%). The filtrate washes were placed in a freezer (−40° F.) for dewaxing overnight. No precipitate was observed the following morning. The 3 washes were combined, and ethanol was recovered by rotary evaporation. The resulting oil was collected in a beaker (161.7 g) and is designated as solution A. Solution A was dark-green/black in color and had a grainy consistency. An attempt to collect the remaining oil in the evaporation flask consisted of adding water and NaOH to the flask and allowing it to rotate at 100 RPM in 40° C. water bath for approximately 20 minutes. The solution was filtered on a Buchner funnel. Then the filtrate was acidified with 3M HCl yielding a white/tan precipitate which was filtered and collected. HPLC indicated that the solid (0.4905 g) was 87.1% THCA (see FIG. 2D).

Ethanol (75 ml) was added to a 120.0 g (~85.5 g THCA) aliquot of solution A to lower viscosity and aid in the dispersion into an aqueous solution. A beaker with 3.27 kg water was brought to pH 11.3 with a 1.8 wt % NaOH solution. The aqueous solution was stirred at 700 RPM (magnetic stirring bar) and 86.2 g of the solution A:ethanol mixture (~23.3 g THCA) was slowly added to the vortex of the solution. Eventually the stirring bar became encumbered. The solution pH dropped to 9.8-10.1 and a green/brown globule formed while stirring and was filtered off with a wide mouth funnel fitted with a coffee filter (Vacuum filtration was very slow due to the small pore size of the filter papers). The mass of wet globule collected was ~84.6 g. The filtrate was found to contain 3.33 g/l THCA by HPLC; an estimated 12 g THCA total. A 2200 ml aliquot of filtrate (~7.3 g THCA), henceforth solution B1, was removed and acidified to pH 8.07 with 3M HCl and allowed to stir in a polypropylene laboratory pitcher. While stirring dark oil started to adhere to the surface of the pitcher (see FIG. 2A). Solution B1 was filtered through a coffee filter and allowed to stir for 10 minutes in a clean polypropylene pitcher; more deposits were made on the plastic while the solution became more and more yellow/white. HCl was added to the filtrate as necessary to keep it around pH 8; solutions were stirred, and more deposits were made on the pitchers. After 4 iterations the solution was significantly less dark and was brought to pH 2.25 with 3M HCl. A precipitate immediately formed and was collected by filtration. A mass of 2.0786 g was recovered and HPLC indicated a purity of 85.9% THCA (2.1% THC); a THCA recovery of 24.5%.

The remaining aliquot (1500 ml) of the 3.33 g/l THCA filtrate (solution B2; ~5 g THCA) was acidified to pH 6.02 and allowed to sit for 2 days in the plastic pitcher in an attempt to adsorb more of the oil impurities. The plastic pitcher had a film of dark oil on it. Solution B2 was filtered through 2 coffee filters and wide mouth funnels to remove any globules not adhered to plastic surfaces. The filtrate was acidified to pH 2.25 and the precipitate was filtered first through a coffee filter to catch any oil and then through vacuum filtration. White precipitate was observed on the coffee filter, but there was not enough to collect and quantify. Vacuum filtration yielded 0.71 g THCA at 86.9% purity; a 14% recovery.

The remaining 64.5 g of solution A (~46 g THCA) was combined with the 84.6 g of wet globule (~11 g THCA) from solution B and 119.1 g of ethanol and heated for 10 minutes at 55° C. to ensure a homogeneous mixture; henceforth solution C. A 53.6 g aliquot of solution C was added slowly to the vortex (1100 RPM; overhead mixer) of 3.98 kg of aqueous NaOH (pH$_o$ 12.56). pH readings became erratic due to adherence of globular oils to the probe. The remainder of solution C was added and stirred at 1100 RPM with an overhead mixer for 34 minutes. The aqueous solution C was well dispersed with minimal globule formation; as apparent after filtration through a coffee filter. The filtrate was separated into two aliquots of 2.08 kg and 2.16 kg, solutions C1 & C2, respectively. Solution C1 was stirred at 800 RPM with an overhead stirrer and acidified to pH 10.4 with 3M HCl. An instantaneous formation of white precipitate was observed followed by slow dissolution of the precipitate and formation of small brown globules. The globules were filtered off with coffee filters and wide mouth funnels. Solution C1 was acidified to pH 9.75 and stirred for 10 minutes before filtering off globules. This was repeated at pH 9.2, 8.6, and 7.7 (FIG. 2). The globule collected in the coffee filter for the pH 9.2 step was 12.0 g and consisted of 4.4 g THC and 1.2 g THCA. At pH 7.7 the globule collected in the coffee filter was 668 mg and contained 325 mg THC and 78 mg THCA. The filtrate collected from the pH 7.7 solution C1 was acidified to pH 2 and placed in the refrigerator to allow the precipitate to settle (settling the precipitate allows for faster filtering due to the ability to decant the multi-liter solution without clogging the filters pores with precipitate). The precipitate recovered the next morning had a mass of 11.92 g and was found to be 76.5% THCA and 11.2% THC. THCA was below quantifiable limits in the filtrate (indicating no more than 1 g of lost THCA in the filtrate). This constitutes a 32.6% THCA recovery.

Solution C2 (~29 g THCA) was allowed to sit overnight at pH 11.1 (see FIG. 2B). A dark film formed on the plastic pitcher. Solution C2 was filtered through coffee filters. The filtrate was poured into a clean plastic pitcher and 2 plastic laboratory funnels were added to increase the surface area. The pitcher was placed in the refrigerator overnight; minimal oil deposited on the funnels and pitcher. Solution C2 was again filtered and then the filtrate (now containing~21 g THCA & 5 g THC) was acidified to pH 8.4 and stirred at 1000 RPM for 13 minutes then filtered. The filtrate was acidified to pH 6.9, stirred, then filtered. Minimal oils were adsorbed to the surface of the pitcher by this point, so the final filtrate was acidified to pH 2.6 and filtered through a Whatman filter paper disc by vacuum filtration. The collected precipitate was green and brown in color. HPLC analysis indicated that only 3.99 g THCA was recovered. This is a recovery of only 14% with a purity of 65%.

Water purification of ethanol extracted cannabis oil is a promising method for fast and low-cost separation of cannabinoid acids. Samples with purities as high as 87% were obtained.

Water-Based Extraction of CBDA:

The effect of particle size on extraction was examined by grinding cannabis flower containing (5.5-7.3% CBDA by mass) with a Fritsch Pulverisette grinder fitted with a 2 mm sieve. The biomass was then sieved (10-80 mesh) on a shaker table. 2.5 g of sieved biomass was added to 50 ml centrifuge tubes and 40 ml pH 11.9 (NaOH) solution was added to the biomass. Additionally, two ground non-sieved samples were prepared with pH 11.9 NaOH or pH 11.9 KOH solutions. The centrifuge tubes were placed in a sonication bath for 10 minutes before being removed and centrifuged at 4300 RPM for 10 minutes. The wash was collected, and fresh pH 11.9 solution was added. The extraction process was completed 6 times with a final rinse of water (no NaOH). Aliquots of the solutions were diluted and analyzed by HPLC. Total CBDA recovery after 6 washes and 1 rinse was unaffected by particle size (76-78%) with the exception of 10-16 mesh particles (the low recovery is thought to be due to the presence of stems in this fraction which contain no measurable amounts of cannabinoid). The rate of extraction was found to not be affected by particle size (FIGS. 3 & 4). 20.1 g of whole dried flower was extracted at a base:acid ratio of 3.4 and the first wash percent solubilization compared to ground non-sieved biomass under the same conditions, vide infra. The whole flower biomass yielded 76% solubilization while the ground material yielded 77% first wash solubilization after 10 minutes of stirring at 900 RPM. Therefore, grinding was determined to be unnecessary, though for ease of material handling it was carried through to the remaining experiments. Extraction with KOH could achieve similar results, but required more washes.

The effect of base:acid ratio (mol NaOH:mol (CBDA+CBGA+THCA) was determined by extraction of 0.3-1 g of ground non-sieved biomass placed in 50 ml centrifuge tubes with 4.4-45.4 ml of NaOH solution ranging in pH from 11.02-13.05. First wash solubilization (after 10 minutes) was determined by HPLC and plotted against base:acid ratio (FIG. 4). Washes carried out with pH 12.0 or lower solution were not as efficient at solubilization than wash at pH 12.3-13.0 when the same base:acid ratio was used (by adjusting volume). A clear maximum solubilization is demonstrated at a base:acid ratio in the 5-12 range. Three additional experiments in which 20 g of biomass were extracted are also shown on the chart. These experiments achieved an average first wash % solubilization of 91±6% at a base:acid ratio of ca. 4.5.

Initial wash time and temperature were screened as a function of pH and for the extraction of ca. 1 g CBDA forward biomass in 20 ml of pH 12.0, 12.5 and 13.0 wash solution. The CBDA concentration in solution are shown (FIG. 5). At all pHs wash time had no discernable effect on solubilization at room temperature. Wash time continued to play no role at elevated temperatures for pH 12.0 experiments. A slight increase was observed for pH 12.5 washes at 33-36° C., and concentrations decreased as time increased at elevated temperatures (at pH 12.5 or above). Heating the solutions only offered modest gains at low pH and had a detrimental effect at high pH. Modulating temperature was not deemed helpful since multiple washes/rinses are required to recover the cannabinoid acid contained in the wash water retained with the biomass. As such, solubilizing a few percent more in the first wash at the risk of thermal degradation would not be considered prudent. Further, the added cost of heating and cooling is deemed wasteful.

Recovery of solubilized cannabinoid acids by repeated washing of biomass was optimized through a series of experiments in which ca. 1 g of CBDA forward biomass was placed in 50 ml centrifuge tubes then 10-30 ml of pH 12.0, 12.5, or 13.0 (NaOH) solution was added. The samples were sonicated at room temperature for 10 minutes, centrifuged and decanted, then rinsed with 10 ml of fresh wash solution (sonicated for ca. 1 minute), and centrifuged again. The rinse was repeated a second time. The results show consistent recovery (82-98%) for pH 12.5 wash at 10, 15, 20, 25 and 30 ml initial washes and pH 13.0 at 10 and 15 ml initial washes (TABLE 2).

TABLE 2

CBDA concentration in wash as a function of pH and volume (left) followed by 2 × 10 ml rinses at the same pH and volume recovered after wash and each rinse (right).

| Initial Wash Vol | Wash (mg/ml) | | | Wash Vol Recovered (ml) | | | CBDA Recovered (mg) | | |
| --- | --- | --- | --- | --- | --- | --- | --- | --- | --- |
| (ml) | pH 12.0 | pH 12.5 | pH 13.0 | pH 12.0 | pH 12.5 | pH 13.0 | pH 12.0 | pH 12.5 | pH 13.0 |
| 10 | 0.273 | 4.085 | 5.322 | 6.0 | 4.3 | 6.4 | 1.64 | 17.57 | 34.06 |
| 15 | 0.494 | 3.127 | 4.246 | 10.5 | 8.2 | 11.6 | 5.19 | 25.64 | 49.26 |
| 20 | 0.478 | 2.508 | 2.227 | 15.3 | 14.1 | 17.0 | 7.32 | 35.36 | 37.86 |
| 25 | 0.573 | 2.337 | 1.882 | 19.9 | 19.2 | 22.4 | 11.40 | 44.88 | 42.15 |
| 30 | 0.570 | 1.884 | 1.456 | 25.2 | 24.1 | 27.8 | 14.35 | 45.41 | 40.48 |

TABLE 2-continued

CBDA concentration in wash as a function of pH and volume (left) followed by 2 × 10 ml
rinses at the same pH and volume recovered after wash and each rinse (right).

| Rinse 1 | Rinse 1 (mg/ml) | | | Rinse 1 Vol Recovered (ml) | | | CBDA Recovered (mg) | | |
|---|---|---|---|---|---|---|---|---|---|
| Vol (ml) | pH 12.0 | pH 12.5 | pH 13.0 | pH 12.0 | pH 12.5 | pH 13.0 | pH 12.0 | pH 12.5 | pH 13.0 |
| 10 | 0.463 | 2.325 | 1.278 | 9.0 | 9.7 | 10.3 | 4.17 | 22.55 | 13.17 |
| 10 | 0.492 | 2.119 | 0.954 | 9.5 | 10.7 | 10.3 | 4.67 | 22.67 | 9.82 |
| 10 | 0.469 | 1.237 | 0.686 | 9.4 | 9.7 | 10.1 | 4.41 | 12.00 | 6.93 |
| 10 | 0.513 | 0.955 | 0.534 | 9.7 | 10.0 | 10.4 | 4.97 | 9.55 | 5.56 |
| 10 | 0.472 | 0.729 | 0.477 | 9.8 | 9.3 | 10.5 | 4.62 | 6.78 | 5.01 |

| Rinse 2 | Rinse 2 (mg/ml) | | | Rinse 2 Vol Recovered (ml) | | | CBDA Recovered (mg) | | |
|---|---|---|---|---|---|---|---|---|---|
| Vol (ml) | pH 12.0 | pH 12.5 | pH 13.0 | pH 12.0 | pH 12.5 | pH 13.0 | pH 12.0 | pH 12.5 | pH 13.0 |
| 10 | 1.744 | 1.332 | 0.470 | 9.7 | 9.8 | 10.6 | 16.91 | 13.05 | 4.98 |
| 10 | 1.778 | 1.035 | 0.362 | 9.4 | 9.8 | 11.1 | 16.71 | 10.14 | 4.02 |
| 10 | 1.534 | 0.583 | 0.267 | 9.7 | 9.4 | 11.2 | 14.88 | 5.48 | 2.99 |
| 10 | 1.477 | 0.397 | 0.207 | 9.8 | 9.4 | 10.4 | 14.47 | 3.73 | 2.16 |
| 10 | 1.242 | 0.356 | 0.174 | 10.4 | 10.1 | 10.6 | 12.92 | 3.60 | 1.84 |

| Initial Wash Vol | Total CBDA Recovered (%) | | | Total Vol Recovered (%) | | | Total CBDA Recovered (mg) | | |
|---|---|---|---|---|---|---|---|---|---|
| (ml) | pH 12.0 | pH 12.5 | pH 13.0 | pH 12.0 | pH 12.5 | pH 13.0 | pH 12.0 | pH 12.5 | pH 13.0 |
| 10 | 35.1% | 82.7% | 81.2% | 82.3% | 79.3% | 91.0% | 22.72 | 53.17 | 52.21 |
| 15 | 41.2% | 90.2% | 97.8% | 84.0% | 82.0% | 94.3% | 26.57 | 58.46 | 63.10 |
| 20 | 42.3% | 81.3% | 75.8% | 86.0% | 83.0% | 95.8% | 26.61 | 52.85 | 47.78 |
| 25 | 47.7% | 92.4% | 77.3% | 87.6% | 85.8% | 96.0% | 30.85 | 58.16 | 49.87 |
| 30 | 49.8% | 87.1% | 73.9% | 90.8% | 87.0% | 97.8% | 31.89 | 55.79 | 47.33 |

Full extraction and recovery were repeated on a larger scale with the 20 g experiments described earlier in this document. Rinses of 150, 200 and 250 ml were carried out. It is clear that the exact rinse volume had little effect on cannabinoid recovery since the first rinse volumes yielded 14.8%, 16.9% and 16.4% while the second rinse volumes yielded 5.0%, 5.0%, and 3.8% for 150 ml, 200 ml and 250 ml, respectively. Instead, the total recovery was more dependent upon the first wash and may be due to variations in starting material (e.g. the initial CBDA mass used in the % recovery calculations may be slightly inaccurate). Cannabinoid acid recovery ranged from 86-97% (Table 3).

TABLE 3

400 ml wash of 20 g WGL biomass followed by 2
rinses at 150 ml, 200 ml and 250 ml on each.

150 ml Rinses

| CBDA Solubilization (98.1%) | 1st Wash | Rinse 1 | Rinse 2 |
|---|---|---|---|
| Vol Added + Unrecovered (ml) | 404.7 | 237.8 | 243.9 |
| Vol Recovered (ml) | 317.8 | 145.1 | 148.8 |
| Vol Unrecovered | 86.9 | 92.7 | 95.1 |
| HPLC Potency | 3.038 | 1.280 | 0.419 |
| CBDA Recovered (mg) | 965.4 | 185.8 | 62.4 |
| CBDA Unrecovered (mg) | 264.0 | 118.7 | 39.9 |
| % CBDA Remaining | 21.1% | 9.5% | 3.2% |
| % CBDA Recovered | 77.0% | 14.8% | 5.0% |
| Cumulative CBDA Recovered | 77.0% | 91.8% | 96.8% |

200 ml Rinses

| CBDA Solubilization (85.7%) | 1st Wash | Rinse 1 | Rinse 2 |
|---|---|---|---|
| Vol Added + Unrecovered (ml) | 400.0 | 302.3 | 301.5 |
| Vol Recovered (ml) | 298.7 | 201.4 | 199.8 |
| Vol Unrecovered | 101.3 | 100.9 | 101.7 |
| HPLC Potency | 2.686 | 1.050 | 0.315 |
| CBDA Recovered (mg) | 802.3 | 211.5 | 63.0 |

TABLE 3-continued 400 ml wash of 20 g WGL biomass followed by 2
rinses at 150 ml, 200 ml and 250 ml on each.

| | | | |
|---|---|---|---|
| CBDA Unrecovered (mg) | 272.1 | 106.0 | 32.0 |
| % CBDA Remaining | 21.7% | 8.5% | 2.6% |
| % CBDA Recovered | 64.0% | 16.9% | 5.0% |
| Cumulative CBDA Recovered | 64.0% | 80.9% | 85.9% |

250 ml Rinses

| CBDA Solubilization (89.6%) | 1st Wash | Rinse 1 | Rinse 2 |
|---|---|---|---|
| Vol Added + Unrecovered (ml) | 401.5 | 334.9 | 340.6 |
| Vol Recovered (ml) | 316.6 | 244.3 | 247.7 |
| Vol Unrecovered | 84.9 | 90.6 | 92.9 |
| HPLC Potency | 2.797 | 0.843 | 0.193 |
| CBDA Recovered (mg) | 885.4 | 205.9 | 47.7 |
| CBDA Unrecovered (mg) | 237.4 | 76.4 | 17.9 |
| % CBDA Remaining | 18.9% | 6.1% | 1.4% |
| % CBDA Recovered | 70.6% | 16.4% | 3.8% |
| Cumulative CBDA Recovered | 70.6% | 87.0% | 90.8% |

An attempt to extract CBD (not CBDA) from 20.1 g of decarboxylated biomass with 449 ml of pH 12.6 solution (conditions analogous to those in described in Table 3) resulted in a first wash solubilization of only 2.8% of the CBD initially present. Furthermore, 3×200 ml rinses with 10-minute soak times yielded a total CBD recovery of only 22±2%.

Precipitation of crude extract (CBDA) by acidification was done with either hydrochloric acid or nitric acid. No difference was observed between the two since the precipitation was pH driven. 1.0-1.5 equivalents of acid (relative to total base) was sufficient for precipitation of the crude extract. The crude extract had CBDA purities on the order of 40-50% and were independent of the amount of acid added. E.g. adding fewer than 1.0 equivalents in an attempt to selectively precipitate either impurities or CBDA yielded crude material with similar purities. Addition of more acid yielded more precipitate of similar purity (up to 1.0-1.5 equivalents). Addition of more than 1.5 equivalents yielded no additional precipitate. Though when the mixture was allowed to sit overnight more white precipitate formed. HPLC analysis of this additional precipitate indicated that it was almost entirely non-cannabinoid/cannabinoid acid. The acidified solution was centrifuged and decanted then rinsed with DI water and centrifuged again before being dried under vacuum at room temperature overnight. HPLC analysis of the acidified solution (pH~4) indicated a loss of ~7 μg CBDA/ml; an approximate 3 orders of magnitude lower than pre-acidification. Crude precipitate left in a relatively wet state began to mold after several days.

Water-Based Extraction of THCA from 'Stripped' $CO_2$ Extracted Biomass:

Further screening of pre-stripped vs non-stripped biomass was done with 300 mg of dried and ground material in 50 ml centrifuges. The pH of NaOH solution was varied from 12.3 to 13.0 and volumes ranged from 9.1-45.4 ml. The mixtures were allowed to sonicate at room temperature for 10 minutes then aliquots taken for HPLC analysis to determine the first wash solubilization as a function of base:acid ratio (FIG. 6).

'Spent' $CO_2$-stripped biomass was aliquoted out to 50 g portions (~6 g THCA). Water (400 ml) and a 40 wt % solution of NaOH (see Tables 4-6) was added to the plant material. The mixture was allowed to stir for 10 minutes at 500-1000 RPM (speed was adjusted to minimize foaming). Solid materials were filtered off with coffee filters. The process was repeated for a total of 4 (Expt A) to 5 (Expts B&C) iterations. A final rinse 2×200 ml with no NaOH was stirred for 1 minute then filtered off. All filtrate was analyzed by HPLC prior to acidification. Acidification to pH 2-3 with HCl, as described above, yielded a precipitate which was filtered off and dried. Both the filtrate and dried material were analyzed by HPLC. All extractions were done at room temperature. The conditions and results for all experiments are shown in Table 4.

Experiment A utilized a NaOH:THCA (mol:mol) ratio of 1:1 (see Table 4). The mass of aqueous extract obtained after the first 10 minutes of stirring is significantly lower than the mass initially added, likely due to adsorption into/on the material. Likewise, the pH of the resulting wash is significantly lower than the solution that was initially added (8.2 vs. 12.7). This may be due to deprotonation of THCA, other acidic functionalities contained within the plant, entrapment inside the plant material, or a combination of those and other factors. The amount of THCA detected in the filtrate increased with each successive wash until a rinse with no added NaOH was conducted for 1 minute. The filtrate from these washes/rinses became progressively lighter in color with the initial washes clogging the pores of the paper filters. Further, with each successive wash/rinse the purity of the THCA harvested increased to a limit of 73%. The 4×10-minute 400 ml aqueous NaOH washes and 2×200 ml×1-minute water rinses yielded~53% extraction efficiency and could have likely been pushed higher if 2 more aqueous NaOH washes had been carried out. It appears that under the conditions of experiment A the solubility limit may be around 0.3 wt % for THCA anions. Upon acidification with HCl a tan/white precipitate formed and was filtered off. The resulting solids were dark in color but got progressively lighter with each wash. FIG. 7 shows the washes/rinse solutions after separation from the plant material (A), after acidification to pH 2-3 (B), precipitate allowed to settle (C), and harvested solids (D). An attempt was made at a later date to strip the colored oily species from the high pH wash by addition of NaCl (A-6,7). Another extraction was carried out with 1:1 NaOH:THCA (A-6) followed by 2×200 ml×1-minute water rinses (A-7). The solutions were separated from the plant material and combined with each other. NaCl (40.2 g) was added to the 789 g aqueous solution and stirred. FIG. 8 shows images of this process. A green/brown oily precipitate formed upon stirring, and the solution became lighter in color. The precipitate was filtered off, collected, and analyzed by HPLC. The filtrate was acidified to pH 2.16 to yield a tan/brown precipitate, filter, collected and analyzed by HPLC. The high pH NaCl precipitate was found to be 31% THCA by mass. The low pH precipitate had a purity of 60%. The total extraction efficiency for experiment A was 57% with an average purity of 64%. The final filtrate (left over after harvesting THCA) contained THCA quantities that were below the limit of quantification (less than 10 mg/400 g wash/rinse; that is <0.001 wt % THCA).

TABLE 4

Conditions and results for aqueous NaOH wash of 'spent' EOG (1:1)

| Experiment-Wash | Mass Plant Material (g) | Mass Water (g) | Mass 40% NaOH (g) | Mass Wash (g) | wt % THCA in Wash | Wash pH | Notes |
|---|---|---|---|---|---|---|---|
| A-1 | 50.0 | 414.0 | 2.0 | 73.3 | 0.11% | 8.22 | Initial THCA ~6.0 g |
| A-2 | 373.1 | 399.4 | 2.1 | 354.4 | 0.16% | 9.23 | |
| A-3 | 398.2 | 393.6 | 2.0 | 376.3 | 0.31% | 10.17 | |
| A-4 | 379.8 | 402.6 | 2.1 | 362.7 | 0.27% | 12.13 | |
| A-5 | 362.7 | 400.0 | 0.0 | 487.0 | 0.16% | 11.87 | 1 min rinse |
| A-6 | 287.4 | 399.6 | 2.0 | 278.4 | — | 12.02 | Extract & wash combined |
| A-7 | 359.0 | 2 × 200 | 0.0 | 510.7 | | | |

| Experiment-Wash | THCA in Wash (g) | Final pH | Mass Solids (g) | THCA % | THCA in Filtrate (g) | % THCA Recovered | Notes |
|---|---|---|---|---|---|---|---|
| A-1 | 0.081 | 2.36 | 0.000 | 62.3% | <0.01 | 0.0% | Sticky oil not able to recover from filter paper |
| A-2 | 0.567 | 2.65 | 0.933 | 45.3% | <0.01 | 7.0% | |
| A-3 | 1.167 | 2.52 | 1.395 | 68.0% | <0.01 | 15.8% | |
| A-4 | 0.979 | 2.22 | 1.352 | 73.2% | <0.01 | 16.5% | |
| A-5 | 0.779 | 2.08 | 1.093 | 72.6% | <0.01 | 13.2% | |
| A-6 | n.d. | 12.02 | 0.317 | 31.2% | n.d. | 1.7% | Added 40.2 g NaCl |
| A-7 | n.d. | 2.16 | 0.240 | 59.9% | n.d. | 2.4% | Acidified NaCl filtrate |
| Total | 3.573 | | 5.330 | 63.7% | | 56.6% | Instrument down. No spent material data |

Experiment B was carried out by the same method as A except NaCl was added to remove plant-based oil impurities prior to precipitation of THCA with HCl (see Table 5). HPLC samples of wash/rinse were taken after filtering off NaCl precipitated solids. Attempts to collect the NaCl precipitated solids were futile; their affinity for the filter paper made acquisition of samples nearly impossible. None-the-less the samples were dissolved in methanol to determine their relative concentration of THCA. Purities of low pH precipitated THCA samples were similar to those of experiment A. However, the total recovery of THCA was significantly lower (21% vs 57%).

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be

TABLE 5

Conditions and results for aqueous NaOH wash of 'spent' material (1:1) with NaCl

| Experiment-Wash | Mass Plant Material (g) | Mass Water (g) | Mass 40% NaOH (g) | Mass Wash (g) | wt % THCA in Wash | Wash pH | Notes |
|---|---|---|---|---|---|---|---|
| B-1 | 49.6 | 393.4 | 2.1 | 124.0 | 0.00% | 7.75 | Initial THCA ~5.9 g |
| B-2 | 308.1 | 393.2 | 2.0 | 388.5 | 0.05% | 9.21 | |
| B-3 | 303.1 | 395.4 | 2.1 | 408.5 | 0.23% | 10.56 | |
| B-4 | 284.8 | 395.4 | 2.1 | 361.6 | 0.10% | 12.00 | |
| B-5 | 310.2 | 394.2 | 2.0 | 398.3 | 0.12% | 12.29 | |
| B-6 | 297.9 | 390.9 | 0.0 | 386.3 | 0.08% | 11.99 | 1 min rinse |

| Experiment-Wash | NaCl Added (g) | % THCA in NaCl | THCA in Wash (g) | Final pH | Recovered Mass (g) | THCA % | Recovery | Notes |
|---|---|---|---|---|---|---|---|---|
| B-1 | 10.0 | 13.7% | 0.000 | 2.98 | 0.022 | 6.3% | 0.0% | |
| B-2 | 10.0 | 45.7% | 0.194 | 2.97 | 0.321 | 38.0% | 2.1% | |
| B-3 | 10.0 | 63.5% | 0.940 | 2.86 | 1.363 | 64.9% | 15.0% | |
| B-4 | 10.0 | 58.0% | 0.362 | 2.62 | 0.027 | 62.8% | 0.3% | |
| B-5 | 10.0 | 40.8% | 0.478 | 2.87 | 0.248 | 67.7% | 2.8% | |
| B-6 | 10.1 | 36.3% | 0.309 | 2.70 | 0.056 | 63.4% | 0.6% | |
| Total | | | 2.282 | | 2.036 | | 20.8% | 0.93 g THCA in spent material |

Experiment C was analogous to experiment B with the exception that the NaOH:THCA ratio was 2:1 (see Table 6). The overall yield was similar to experiment B (18% vs. 21%). As in experiment B the NaCl precipitated solids contained THCA. It is likely that the yields would be higher without addition of NaCl prior to acidification. Purities, were significantly higher (86%) with extractions from experiment C and experiment B.

included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise

TABLE 6

Conditions and results for aqueous NaOH wash of 'spent' material (2:1) with NaCl

| Experiment-Wash | Mass Plant Material (g) | Mass Water (g) | Mass 40% NaOH (g) | Mass Wash (g) | wt % THCA in Wash | Wash pH | Notes |
|---|---|---|---|---|---|---|---|
| C-1 | 50.6 | 395.3 | 4.1 | 110.9 | 0.00% | 8.37 | Initial THCA ~6.1 g |
| C-2 | 329.3 | 395.2 | 4.1 | 233.7 | 0.00% | 10.70 | |
| C-3 | 444.4 | 393.4 | 4.1 | 474.5 | 0.07% | 12.34 | |
| C-4 | 301.1 | 391.4 | 4.1 | 400.2 | 0.08% | 12.58 | |
| C-5 | 282.8 | 393.5 | 4.1 | 398.8 | 0.09% | 12.66 | |
| C-6 | 260.2 | 392.9 | 0.0 | 406.5 | 0.08% | 12.38 | 1 min rinse |

| Experiment-Wash | NaCl Added (g) | % THCA in NaCl | THCA in Wash (g) | Final pH | Recovered Mass (g) | THCA % | Recovery | Notes |
|---|---|---|---|---|---|---|---|---|
| C-1 | 10.0 | 27.8% | 0.000 | 2.85 | 0.003 | 1.6% | 0.0% | |
| C-2 | 10.0 | 22.1% | 0.011 | 2.66 | 0.048 | 32.3% | 0.3% | |
| C-3 | 10.0 | 31.6% | 0.323 | 2.96 | 0.344 | 62.4% | 3.5% | |
| C-4 | 10.0 | 46.0% | 0.325 | 2.44 | 0.372 | 80.2% | 4.9% | |
| C-5 | 10.0 | 30.5% | 0.373 | 2.58 | 0.410 | 86.3% | 5.8% | |
| C-6 | 10.0 | 27.5% | 0.311 | 2.72 | 0.272 | 85.3% | 3.8% | |
| Total | | | 1.343 | | 1.449 | | 18.3% | 1.5 g THCA in spent material |

The invention claimed is:

1. A method of extracting cannabinoids acids from cannabis-containing plant material that does not require use of a method selected from the group consisting of dewaxing, recovery of solvent, and distillation, said method including the steps of:
   mixing a cannabis-containing plant material with an aqueous base solution to form a basic mixture;
   separating the aqueous base solution from the plant material;
   adding a salt to the basic mixture;
   acidifying the basic mixture to form a precipitate; and
   removing the precipitate;
   whereby the method does not include a dewaxing step or solvent collection.

2. The method of claim 1 whereby the plant material is mixed with the base to form a mixture having a pH of at least 10.

3. The method of claim 1 whereby the base is a strong organic or inorganic base.

4. The method of claim 3 whereby the base is NaOH.

5. The method of claim 1 whereby the separating step comprises stirring or agitating the basic mixture.

6. The method of claim 1 whereby the separating step comprises allowing the mixture to sit at least 10 minutes.

7. The method of claim 6 whereby the separating step comprises allowing the mixture to sit overnight.

8. The method of claim 1 further including the step of:
   filtering the hydrophobic impurities from the basic cannabinoid extract to form a filtered extract.

9. The method of claim 1 whereby the acidifying step comprises lowering the pH of the basic mixture to 9 or lower prior to the precipitate removal step.

10. The method of claim 9 whereby the pH of the basic mixture is lowered to 6 or below.

11. The method of claim 9 whereby the pH of the basic mixture is lowered by adding an inorganic or an organic acid to the basic mixture.

12. The method of claim 8 further including the steps of:
    collecting the filtered impurities with an ethanol wash to form collected impurities; and
    distilling the collected impurities to form terpenes and neutral cannabinoids.

13. The method of claim 1 whereby the salt is a halide salt.

14. The method of claim 13 whereby the salt is NaCl.

* * * * *